United States Patent
Demay et al.

(10) Patent No.: US 6,350,932 B1
(45) Date of Patent: Feb. 26, 2002

(54) VITAMIN D RECEPTOR ABLATED MICE

(75) Inventors: Marie Demay, Wellesley, MA (US); Yan Chun Li, Chicago, IL (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/143,012

(22) Filed: Aug. 28, 1998

Related U.S. Application Data (60) Provisional application No. 60/057,252, filed on Aug. 29, 1997.

(51) Int. Cl.$^7$ .................. A01K 67/027; A01K 67/00; G01N 33/00; C12N 5/00; C12N 15/00
(52) U.S. Cl. .................. 800/3; 800/8; 800/9; 800/13; 800/14; 800/18; 435/325; 435/354; 435/455; 435/463; 514/880
(58) Field of Search .................. 800/3, 8, 9, 11, 800/13, 18, 14; 514/880, 885; 435/325, 354, 435, 463, 455

(56) References Cited

U.S. PATENT DOCUMENTS

| | | | |
|---|---|---|---|
| 5,174,986 A | * 12/1992 | Berns | 424/9 |
| 5,430,579 A | * 7/1995 | Cesaro | 424/114 |
| 5,486,509 A | * 1/1996 | Jimenez et al. | 514/167 |

OTHER PUBLICATIONS

R.J. Wall, Theriogenology, 45:57–68, 1996.*
A. Colman, Am J. Clin. Nutr., 63:639S–645S, 1996.*
Palmiter et al., Proc. Natl. Acad. Sci., USA, 88:478–482, 1991.*
Nakajima et al., Biochem. Biophys. Res. Commun., 197:478–485, 1993.*
Li et al., Endocrinology, 138:2347–2353, 1997.*
Yoshizawa et al., Nature Genetics, 16:391–396, 1997.*
Hawa et al., Clin. Endocrinology, 45:85–92, 1996.*
Kamei et al. Cloning and Sequencing of the Gene Encoding the Mouse Vitamin D Receptor. Gene. 1995, vol. 152, pp. 281–282.
Capecchi. Targeted Gene Replacement. Scientific American. Mar. 1994, vol. 270, No. 3, pp. 34–41.
Westphal. Transgenic Mammals and Biotechnology. FASEB Journal. 1989, vol. 3, pp. 117–120.
Balsan, Sonia et al., "Long–Term nocturnal Calcium Infusion Can Cure Rickets and Promote Normal Mineralization Hereditary Resistance to 1,25–Dihydroxyvitamin D," *The Journal of Clinical Investigation*, vol. 77. No. 5, (May, 1986).
Bikle, Daniel D. et al., "Regulation of 1,25–Dihydorxyvitamin D Production in Human Keratinocytes by Interferon–γ," *Endocrinology*, vol. 124, No. 2 (Feb., 1989).
Bikle, Daniel et al., "Vitamin D, Calcium, and Epidermal Differentiation," *Endocrine Reviews*, vol. 14, No. 1, (1993).

Bradley, Allan et al., "Modifying the Mouse: Design and Desire," *BioTechnology*, vol. 10, (May 1992).
Dostal, Lori A. et al., "Effect of Vitamin $D_3$ on Duodenal Calcium Absorption in vivo During Early Development," *American Journal of Physiology: Endocrinology and Metabolism*, vol. 9, No. 5, (May 1984).
Elaroussi, Mahmoud A. et al., "The Role of Vitamin D in Chorioallantoic Membrane Calcium Transport," *Biochemica et Biophysica Acta*, vol. 1192 (1994).
Halloran, Bernard P. et al., "Effect of Vitamin D Deficiency on Skeletal Development During Early Growth in the Rat" *Archives of Biochemistry and Biophysics*, vol. 209, No. 1, pp 7–14, (1981).
Johnson, Julie A. et al., "Ontogeny of the 1,25–Dihydorxyvitamin $D_3$ Receptor in Fetal Rat Bone," *Journal of Bone and Mineral Research*, vol. 11, No. 1., Nov. 1996.
Li, Yan Chun et al., "Cloning and Characterization of the Vitamin D Receptor from *Xenopus laevis*" *Endocrinology*, 138:6 (1997).
Manolagas, Stavros C. et al., "Immunomodulating Properties of 1,25–Dihydoxyviatmin $D_3$," *Kidney International* vol. 38, Supplement 29 (1990).
Miller, Scott C. et al., "Studies on the Role of Vitamin D in Early Skeletal Development Mineraliztion, and Growth in Rats," *Calcified Tissue International*, vol. 35, No. 4–5 (1983).
Norman, Anthony et al., "Vitamin Deficiency Inhibits Pancreatic Secretion of Insulin," *Science*, vol. 209, (Aug., 1980).
Pavlovitch, Galoppin et al., "Alterations of Rat Epidermin Provoked by Chronic Vitamin D Deficiency," *American Journal of Physiology*, vol. 247, No. 2, (Aug. 1984).
Reichrath, Schilli et al., "Hair Follicle Expression of 1,25–Dihydroxyvitamin $D_3$ Receptors during the Murine Hair Cycle, " *British Journal of Dermatology*, vol. 131, No. 4 (Oct. 1994).

(List continued on next page.)

*Primary Examiner*—Deborah J. R. Clark
*Assistant Examiner*—Janet M. Kerr
(74) *Attorney, Agent, or Firm*—Fish & Richardson P.C.

(57) ABSTRACT

A transgenic mouse containing disruptions in both vitamin D alleles and lacking vitamin D receptor activity is described. The transgenic mouse displays perioral and periorbital alopecia, hypocalcemia, hypophosphatemia, and bone demineralization. The transgenic mouse is useful for screening treatments for a number of conditions associated with vitamin D receptor related disorders including skin disorders, immune system disorders, and proliferative disorders.

10 Claims, 2 Drawing Sheets

OTHER PUBLICATIONS

Silver, Justin et al., "Regulation by Vitamin D Metabolites of Messenger Ribonucleic Acid for Preproparathryoid Hormone in Isolated Bovin Parathyroid Cells" *Proceeding of the National Academy of Sciences* vol. 82, No. 12, (Jun. 1985).

Strugnell, Stephen et al., "The Vitamin D receptor–Structure and Transcriptional Activation," *Proceedings of the Society for Experimental Biology and Medicine*, vol. 215, No. 2 (Jun. 1997).

Stump, Walter et al., "Target Cells for 1,25–Dihydroxyvitamin $D_3$ in Intestinal Tract, Stomach, Kidney, Skin, Pituitary, and Parathyroid," *Science* vol. 206, No. 7, (Dec. 1979).

Tieder, S. Beer et al., Vitamin D Resistant Rickets with Alopeciaa: A Form of End Organ Resistance to 1.25 Dihydroxy Vitamin D, "*Clinical Endocrinology*" vol. 14, pp 395–402 (1981).

Tuan, Rocky S. et al., "Developmental Expression and vitamin D Regulation Calbindin–$D_{28K}$ in Chick Embryonic Yolk Sac Endoderm," *The Journal of Nutrition*, vol. 126, No. 4S (Apr. 1996).

* cited by examiner

VITAMIN D RECEPTOR ABLATED MICE

CROSS REFERENCE TO RELATED APPLICATIONS

This application claims priority from U.S. provisional patent application Ser. No. 60/057,252 filed Aug. 29, 1997, incorporated herein by reference.

STATEMENT AS TO FEDERALLY SPONSORED RESEARCH

Work described herein was supported by funding from the National Institute of Health. The United States Government has certain rights in the invention.

FIELD OF THE INVENTION

The invention relates to animals in which the vitamin D receptor is misexpressed and methods of using such animals or cells derived therefrom, e.g., in methods of evaluating treatments for skin disorders, immune disorders and proliferation-related disorders.

BACKGROUND OF THE INVENTION

The vitamin D receptor (VDR), is a nuclear receptor which heterodimerizes with the retinoid X receptor and interacts with specific DNA sequences on target genes, regulating their expression. The VDR is evolutionary well conserved and is expressed early in development in amphibians (Li Y. et al., (1997) Endocrinology 138:2347–2353), mammals (Johnson J. A. et al., (1996) J. Bone Miner. Res. 11:56–61), and birds (Elaroussi M. A. et al., (1994) Biochim. Biophys. Acta 1192:1–6; and Tuan R. S. and Suyama E., (1996) J. Nutr. 126:1308S–1316S). The VDR is expressed in tissues involved in mineral ion homeostasis, such as the intestine, the skeleton, and the parathyroid glands, as well as in tissues not thought to play a role in mineral ion homeostasis, such as the epidermis and the pancreas (Stumpf W. E. et al., (1979) Science 206:1188–1190).

Its principal ligand, 1,25-dihydroxyvitamin D is a steroid hormone that plays a role in mineral ion homeostasis. Insights into the physiological actions of 1,25-dihydroxyvitamin D have been obtained from studies in vitamin D deficient animals (Dostal L. A. and Toverud S. U., (1984) Am J. Physiol. 246:G528–G534; Halloran B. P. and DeLuca H. F., (1981) Arch. Biochem. Biophys. 209:7–14; Mathews C. H. E. et al., (1986) Am. J. Physiol. 250:E725–E730; Miller S. C. et al., (1983) Calcif. Tissue Int. 35:455–460; and Underwood J. L. and DeLuca H. F., (1984) Am. J. Physiol. 246:E493–E498) as well as in humans with VDR mutations (Balsan S. et al., (1986) J. Clin. Invest. 77:1661–1667; and Beer S. et al., (1981) Clin. Endocrinol. 14:395–402). These investigations have demonstrated that 1,25-dihydroxyvitamin D plays an important role in intestinal calcium absorption and that animals lacking in active hormone or its nuclear receptor develop hypocalcemia, rickets, osteomalacia, and hyperparathyroidism.

1,25-dihydroxyvitamin D is also believed to inhibit parathyroid hormone synthesis in the parathyroid gland (Silver J. et al., (1985) Proc. Natl. Acad. Sci. USA 82:4270–4273), blocking interleukin-2 production in activated lymphocytes (Manolagas S. C. et al., (1990) Kidney Int. 29:S9–S16), stimulating insulin secretion in the pancreas (Norman A. W. et al., (1980) Science 209:823–825), and decreasing proliferation and inducing differentiation of keratinocytes in the epidermis (Bikle D. D. et al., (1988) Endocrinology 124:655–660).

SUMMARY OF THE INVENTION

In general, the invention features, a non-human animal, in which the gene encoding the vitamin D receptor is misexpressed.

In preferred embodiments the animal, which is preferably a transgenic animal, is a mammal, e.g., a nonhuman primate or a swine, e.g., a miniature swine, a monkey, a goat, or a rodent, e.g., a rat, but preferably a mouse.

In preferred embodiments, expression of the gene encoding the vitamin D receptor is decreased as compared to the wild-type mouse. For example, the levels of the vitamin D receptor can be suppressed by, at least, 50, 60, 70, 80 or 90% or 100% as compared to the wild-type mouse.

In preferred embodiments, misexpression of the gene encoding the vitamin D receptor is caused by disruption of the vitamin D receptor gene. For example, the vitamin D receptor gene can be disrupted through removal of DNA encoding all or part of the receptor, e.g., removal of all or part of a zinc-finger domain, e.g., the second zinc-finger of the DNA-binding domain of the receptor.

In preferred embodiments, the animal can be heterozygous or homozygous for a misexpressed VDR gene, e.g., it can be a transgenic animal heterozygous or homozygous for a VDR transgene.

In preferred embodiments, the animal is a transgenic mouse with a transgenic disruption of the VDR, preferably an insertion or deletion, which inactivates the gene product.

Figure 1:
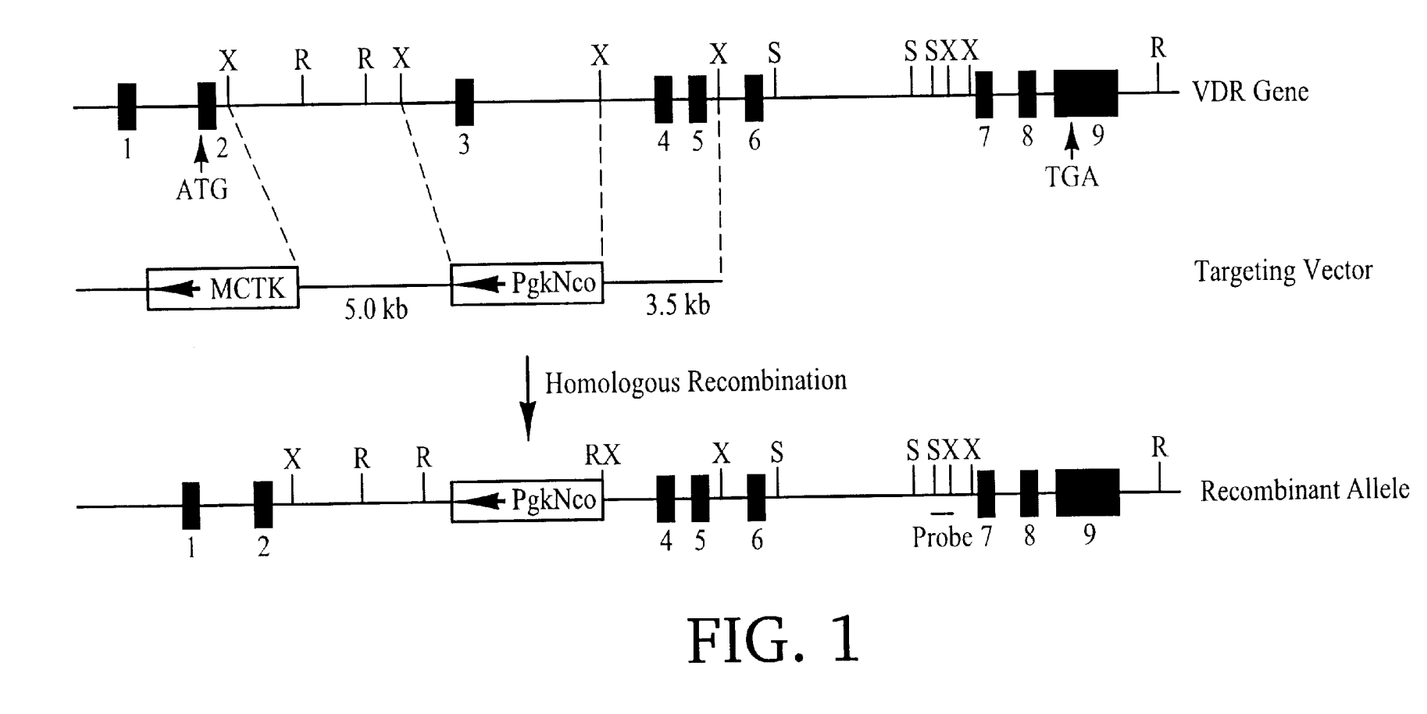
FIG. 1 is a schematic representation of the targeting strategy for the disruption of the VDR gene. On the top, a schematic representation of the VDR gene is shown. In the middle, the targeting vector is depicted and in the bottom the recombinant allele is shown, in which the VDR gene was disrupted by the neomycin resistance gene.

In another aspect, the invention features, a nucleic acid sequence which, when introduced into an animal or cell, results in the misexpression of the VDR gene in the animal or cell. In preferred embodiments, the nucleic acid sequence, includes a VDR sequence which includes a disruption, e.g., an insertion or deletion and preferably the insertion of a marker sequence. For example, nucleic acid sequence can be the targeting construct, shown in FIG. 1.

In another aspect, the invention features, a method of evaluating a treatment for a skin disorder. The method includes: administering the treatment to a VDR misexpressing animal or a cell therefrom; and determining the effect of the treatment on a parameter related to the skin disorder, to thereby evaluate the treatment for the skin disorder. The method may be performed in vivo or in vitro.

In preferred embodiments, the animal or cell is an animal or cell described herein.

In preferred embodiments, the method further includes determining the effect of the treatment on the levels, e.g., plasma levels, of calcium in the animal or cell.

In preferred embodiments, the skin disorder is a proliferative skin disorder. For example, the skin disorder can be a hyperproliferative skin disorder, e.g., psoriasis, squamus cell carcinoma, alopecia and the like.

In preferred embodiments, the effect of the treatment on the proliferative skin disorder can be determined by measuring such parameters as the thickness of the keratinocyte layer or the number and size of papules present on the skin of the animal; cell growth; tumor growth, weight or invasiveness; life span; tissue morphology; weight; or the expression of a gene related to cell proliferation.

In preferred embodiments, the effect of the treatment on alopecia can be determined by measuring such parameters as hair growth (in terms of the number, thickness, or growth rate of hairs), hair follicle morphology, or the pattern of hair growth.

In preferred embodiments, the method uses a transgenic mouse in which the expression of the VDR is inhibited.

In preferred embodiments, the method uses a cell derived from a transgenic mouse in which the expression of the VDR is inhibited.

In another aspect, the invention features, a method of evaluating a treatment for an immune disorder or condition. The method includes: administering the treatment to a VDR misexpressing animal or a cell therefrom; and determining the effect of the treatment on a parameter related to the immune disorder or condition, to thereby evaluate the treatment for the immune disorder or condition. The method may be performed in vivo or in vitro.

In preferred embodiments, the animal or cell is an animal or cell described herein.

In preferred embodiments, the method further includes determining the effect of the treatment on the levels, e.g., plasma levels, of calcium in the animal or cell.

In preferred embodiments, the effect of the treatment on the immune disorder or condition can be determined by measuring a parameter such as: the presence, function, or morphology of T cells or their progenitors; the presence, function, or morphology of B cells or their progenitors; the presence, function, or morphology of natural killer cells or their progenitors; resistance to infection; life span; body weight; the presence, function, or morphology of tissues or organs of the immune system; or the expression of a gene related to an immune disorder or condition.

In preferred embodiments, the method uses a transgenic mouse in which the expression of the VDR is inhibited.

In preferred embodiments, the method uses a cell derived from a transgenic mouse in which the expression of the VDR is inhibited.

In another aspect, the invention features, a method of evaluating a treatment for promoting acceptance of a graft. The method includes: providing an animal, in which the gene encoding the vitamin D receptor is misexpressed; (optionally) introducing a graft tissue into the animal; administering the treatment to the animal; and determining the effect of the treatment on the acceptance of the graft by the animal to, thereby, evaluate the treatment for promoting acceptance of a graft.

The graft tissue can be an allograft or a xenograft. Allografts can be partially or fully mismatched. E.g., matched allografts can be matched at one or more class I locus, one or more class II locus, or one or more minor antigen locus. Xenografts can be primate, e.g., monkey, or swine, e.g., miniature swine, or dog grafts. Grafts, allografts or xenografts, can be an organ, e.g., a lung, kidney, heart, liver, or endocrine tissue, e.g., pancreatic tissue, e.g., pancreatic islets, connective tissue, bone, skin, or bone marrow.

In preferred embodiments, the animal is an animal described herein.

In preferred embodiments, the method further includes determining the effect of the treatment on the levels, e.g., plasma levels, of calcium in the animal.

In preferred embodiments, the method further includes administering a second treatment to the animal. For example, an immunosuppressant, e.g., Azathioprine, Cyclosporine, Muromonab-CD3, FK506, rapamycin or Bromocriptine Mesylate can be administered with the treatment. The second treatment can be a treatment which induces tolerance to a graft, e.g., the introduction of donor bone marrow cells into the recipient of the graft.

In preferred embodiments, the effect of the treatment in promoting acceptance of a graft can be determined by measuring a parameter such as: acceptance of the graft; the presence, function, or morphology of T cells or their progenitors; the presence, function, or morphology of B cells or their progenitors; the presence, function, or morphology of natural killer cells or their progenitors; resistance to infection; life span; body weight; or the presence, function, or morphology of tissues or organs of the immune system; or the ability to exhibit immunological tolerance to the graft tissue.

In preferred embodiments, the method uses a transgenic mouse in which the expression of the VDR is inhibited.

In another aspect, the invention features, a method of evaluating a treatment for an autoimmune disease. The method includes: administering the treatment to a VDR misexpressing animal or a cell therefrom; and determining the effect of the treatment on a parameter related to the autoimmune disease, to thereby evaluate the treatment for the autoimmune disease. The method may be performed in vivo or in vitro.

In preferred embodiments, the method further includes providing an animal or cell model for the autoimmune disease, e.g., a disorder described herein. A preferred animal model is the NOD mouse.

In preferred embodiments, the disorder is an autoimmune disease such as rheumatoid arthritis, e.g., juvenile rheumatoid arthritis, psoriatic arthritis, psoriasis, leprosy reversal reactions, erythema nodosum leprosum, autoimmune uveitis, multiple sclerosis, allergic encephalomyelitis, systemic lupus erythematosus, acute necrotizing hemorrhagic encephalopathy, idiopathic bilateral progressive sensorineural hearing loss, aplastic anemia, pure red cell anemia, idiopathic thrombocytopenia, polychondritis, scleroderma, Wegener's granulomatosis, chronic active hepatitis, myasthenia gravis, Stevens-Johnson syndrome, idiopathic sprue, lichen planus, Crohn's disease, Graves ophthalmopathy, sarcoidosis, primary biliary cirrhosis, diabetes, e.g., primary juvenile diabetes, dry eye associated with Sjögren's syndrome, uveitis posterior, or interstitial lung fibrosis.

In preferred embodiments, the animal or cell, is an animal or cell described herein.

In preferred embodiments, the method further includes determining the effect of the treatment on the levels, e.g., plasma levels, of calcium in the animal or cell.

In preferred embodiments, the effect of the treatment on the autoimmune disease can be determined by measuring a parameter such as: the presence, function, or morphology of T cells or their progenitors; the presence, function, or morphology of B cells or their progenitors; the presence, function, or morphology of natural killer cells or their progenitors; resistance to infection; life span; body weight; or the presence, function, or morphology of tissues or organs of the immune system; acceptance of a graft, preferably a syngeneic graft, e.g., syngeneic pancreatic cells; or, generally, the ability of the animal or cell to recognize the animal's or cell's own antigens.

In preferred embodiments, the method uses a transgenic mouse in which the expression of the VDR is inhibited.

In preferred embodiments, the method uses a cell derived from a transgenic mouse in which the expression of the VDR is inhibited.

In another aspect, the invention features, a method of evaluating a treatment for a condition characterized by unwanted cell proliferation, e.g., malignant growth. The method includes: providing an animal or a cell, in which the gene encoding the vitamin D receptor is misexpressed; (optionally) inducing or introducing a proliferative cell, e.g., a malignant cell, in the animal (or inducing a proliferative state, e.g., malignancy in a cell); administering the treatment to the animal or cell; and determining the effect of the treatment on a parameter related to a condition characterized by unwanted cell proliferation, to thereby evaluate a treatment for the condition characterized by unwanted cell proliferation. The method may be performed in vivo or in vitro.

In preferred embodiments, the animal or cell is an animal or cell described herein.

In preferred embodiments, the method further includes determining the effect of the treatment on the levels, e.g., plasma levels, of calcium in the animal or cell.

In preferred embodiments, the effect of the treatment on the condition characterized by unwanted cell proliferation can be determined by measuring such parameters as the cell growth; tumor growth, weight or invasiveness; life span; tissue morphology; weight; or the expression of a gene related to unwanted cell proliferation.

In preferred embodiments, the method uses a transgenic mouse in which the expression of the VDR is inhibited.

In preferred embodiments, the method uses a cell derived from a transgenic mouse in which the expression of the VDR is inhibited.

In another aspect, the invention features, a method of evaluating a treatment suitable for modulating, e.g., inhibiting or promoting, hair growth. The method includes: administering the treatment to a VDR misexpressing transgenic mouse, e.g., a knockout mouse; and determining the effect of the treatment on a parameter related to hair growth to, thereby, evaluate the treatment suitable for modulating hair growth. The evaluation can include determining the effect on: hair growth (in terms of the number, thickness, or growth rate of hairs), hair follicle morphology, or the pattern of hair growth.

In another aspect, the invention features, a method of evaluating a treatment for psoriasis. The method includes: administering the treatment to a VDR misexpressing transgenic mouse, e.g., a knockout mouse; and determining the effect of the treatment on a parameter related to psoriasis, to, thereby, evaluate the treatment for psoriasis.

In another aspect, the invention features, a method of treating hirsutism or hypertrichosis in a subject, e.g., a human. The method includes inhibiting the activity of VDR in the subject's keratinocytes by, for example, disrupting the gene encoding the vitamin D receptor in the subject's keratinocytes, or by administering, to the subject, a 1,25 dihydroxyvitamin D analogue, e.g., an antagonist, an anti-VDR antibody, e.g., an anti-VDR intrabody, or an anti-sense nucleic acid which inhibits the expression of the VDR.

In preferred embodiments, the gene encoding the vitamin D receptor is disrupted by introduction into the keratinocytes of the subject of a nucleic acid sequence, which when introduced into the subject's keratinocytes, results in the misexpression of the VDR gene in the subject's keratinocyres.

In another aspect, the invention features, a cell, or a purified preparation of cells, from a VDR misexpressing animal, e.g., a VDR misexpressing animal described herein. In preferred embodiments, the cell is a transgenic cell, in which the gene encoding the vitamin D receptor is misexpressed. The cell, preferably a transgenic cell can be a keratinocyte, a monocyte, a pancreatic cell or a lymphocyte.

In preferred embodiments, the cell is heterozygous or homozygous for the transgenic mutant gene.

As used herein, a "transgenic animal" is an animal, e.g., a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, e.g., by microinjection, transfection or infection, e.g., by infection with a recombinant virus. The term genetic manipulation is directed to the introduction of a recombinant DNA molecule. This molecule may be integrated within a chromosome, or it may be extrachromosomally replicating DNA.

As used herein, the term "rodent" refers to all members of the phylogenetic order Rodentia.

As used herein, the term "transgenic cell" refers to a cell containing a transgene.

As used herein, the term "misexpression" refers to a non-wild type pattern of gene expression. Expression as used herein includes transcriptional, post transcriptional, e.g., mRNA stability, translational, and post translational stages. Misexpression includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus. Misexpression includes any expression from a transgenic nucleic acid. Misexpression includes the lack or non-expression of a gene or transgene, e.g., that can be induced by a deletion of all or part of the gene or its control sequences.

As used herein, the term "knockout" refers to an animal or cell therefrom, in which the insertion of a transgene disrupts an endogenous gene in the animal or cell therefrom. This disruption can essentially eliminate VDR in the animal or cell.

As used herein, the term "marker sequence" refers to a nucleic acid sequence that (a) is used as part of a nucleic acid construct (e.g., the targeting construct) to disrupt the expression of the gene of interest (e.g., the vitamin D receptor gene) and (b) is used to identify those cells that have incorporated the targeting construct into their genome. For example, the marker sequence can be a sequence encoding a protein which confers a detectable trait on the cell, such as an antibiotic resistance gene, e.g., neomycin resistance gene, or an assayable enzyme not typically found in the cell, e.g., alkaline phosphatase, horseradish peroxidase, luciferase, beta-galactosidase and the like.

As used herein, "disruption of a gene" refers to a change in the gene sequence, e.g., a change in the coding region. Disruption includes: insertions, deletions, point mutations, and rearrangements, e.g., inversions. The disruption can occur in a region of the native vitamin D receptor DNA sequence (e.g., one or more exons) and/or the promoter region of the gene so as to decrease or prevent expression of the gene in a cell as compared to the wild-type or naturally occurring sequence of the gene. The "disruption" can be induced by classical random mutation or by site directed methods. Disruptions can be transgenically introduced. The deletion of an entire gene is a disruption. The disruption can, e.g., occur in a region of the VDR which mediates heterodimerization, in a region which mediated DNA binding, e.g., a zinc-finger domain, or in a region which mediates ligand binding. Preferred disruptions reduce VDR levels to about 50% of wild type, in heterozygotes or essentially eliminate VDR in homozygotes.

As used herein, "administering a treatment to an animal or cell" is intended to refer to dispensing, delivering or applying a treatment to an animal or cell. In terms of the therapeutic agent, the term "administering" is intended to refer to dispensing, delivering or applying the therapeutic agent to an animal by any suitable route for delivery of the therapeutic agent to the desired location in the animal, including delivery by either the parenteral or oral route, intramuscular injection, subcutaneous/intradermal injection, intravenous injection, buccal administration, transdermal delivery and administration by the intranasal or respiratory tract route. The term "administering" is further intended to refer to bringing the therapeutic agent into close proximity with a cell, such that the therapeutic agent can exert its effects on the cell.

As used herein, "purified preparation" is a preparation which includes at least 10, more preferably 50, yet more preferably 90% by number or weight of the subject cells.

As used herein, the term "psoriasis" is art recognized and refers to a chronic, occasionally acute, non contagious, relapsing skin disease, characterized by distinct reddish, slightly raised plaques or papules (small, round skin elevations) covered with scales. Psoriasis ordinarily involves the scalp, the elbows, the knees, the back, and the buttocks. Occasionally, the disease can be generalized. Psoriasis is the result of an abnormally high rate of mitosis in epidermal cells that may be related to a substance carried by the blood, a defect in the immune system or a virus.

As used herein, the term "alopecia" is art recognized and refers to the loss of hair, wool or feathers, e.g., baldness.

As used herein, the terms "hirsutism" and "hypertrichosis" are conditions characterized by excessive growth of hair. The conditions can occur in females and children, with a distribution of hair similar to that found in adult males. Hirsutism is the result of the conversion of vellus hair to large terminal hair as a result of higher than normal levels of androgens. Hirsutism may be familial or idiopathic. Hypertrichosis is a diffuse increase in body hair which may be idiopathic or may result from hormonal disorders or drugs.

The methods of the invention allow rapid and efficient screening of treatments for skin disorders, immune disorders and proliferation-related disorders.

Other features and advantages of the invention will be apparent from the following detailed description, and from the claims.

DETAILED DESCRIPTION

The drawings are first briefly described.

BRIEF DESCRIPTION OF THE DRAWINGS

FIG. 2A–C is a series of graphs depicting the growth and serum chemistries of the VDR knockout mice.

PREPARATION OF VDR TARGETING CONSTRUCTS

The VDR nucleic acid sequence to be used in producing the targeting construct is digested with a particular restriction enzyme selected to digest at a location(s) such that a new DNA sequence encoding a marker gene can be inserted in the proper position within this VDR nucleic acid sequence. The marker gene should be inserted such that it can serve to prevent expression of the native gene. As VDR forms a heterodimer with other nuclear receptors, e.g., with RXR, lesions which result in dominant negative mutations should be avoided. The position will depend on various factors such as the restriction sites in the sequence to be cut, and whether an exon sequence or a promoter sequence, or both is (are) to be interrupted (i.e., the precise location of insertion necessary to inhibit VDR gene expression). In some cases, it will be desirable to actually remove a portion or even all of one or more exons of the gene to be suppressed so as to keep the length of the targeting construct comparable to the original genomic sequence when the marker gene is inserted in the targeting construct. In these cases, the genomic DNA is cut with appropriate restriction endonucleases such that a fragment of the proper size can be removed.

The marker sequence can be any nucleic acid sequence that is detectable and/or assayable. For example, the marker gene can be antibiotic resistance gene or other gene whose expression in the genome can easily be detected. The marker gene can be linked to its own promoter or to another strong promoter from any source that will be active in the cell into which it is inserted; or it can be transcribed using the promoter of the VDR gene. The marker gene can also have a polyA sequence attached to the 3' end of the gene; this sequence serves to terminate transcription of the gene. For example, the marker sequence can be a protein that (a) confers resistance to antibiotics or other toxins; e.g., ampicillin, tetracycline, or kanamycin for prokaryotic host cells, and neomycin, hygromycin, or methotrexate for mammalian cells; (b) complements auxotrophic deficiencies of the cell; or (c) supplies critical nutrients not available from complex media.

After the VDR DNA sequence has been digested with the appropriate restriction enzymes, the marker gene sequence is ligated into the VDR DNA sequence using methods known to the skilled artisan and described in Sambrook et al., Molecular Cloning A Laboratory Manual, 2nd Ed., ed., Cold Spring Harbor Laboratory Press: 1989, the contents of which are incorporated herein by reference.

Preferably, the ends of the DNA fragments to be ligated are compatible; this is accomplished by either restricting all fragments with enzymes that generate compatible ends, or by blunting the ends prior to ligation. Blunting is performed using methods known in the art, such as for example by the use of Klenow fragment (DNA polymerase I) to fill in sticky ends.

The ligated targeting construct can be inserted directly into embryonic stem cells, or it may first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

Construction of Transgenic Mice Transfection of Embryonic Stem Cells

Mouse embryonic stem cells (ES cells) can be used to generate the transgenic (e.g., knockout) VDR mice. Any ES cell line that is capable of integrating into and becoming part of the germ line of a developing embryo, so as to create germ line transmission of the targeting construct is suitable for use herein. For example, a mouse strain that can be used for production of ES cells, is the 129J strain. A preferred ES cell line is murine cell line D3 (American Type Culture Collection catalog no. CRL 1934). The cells can be cultured and prepared for DNA insertion using methods known in the art and described in Robertson, Teratocarcinomas and Embryonic Stem Cells: A Practical Approach, E. J. Robertson, ed. IRL Press, Washington, D.C., 1987, in Bradley et al., Current Topics in Devel. Biol., 20:357–371, 1986 and in Hogan et al., Manipulating the Mouse Embryo: A Laboratory Manual, Cold Spring Harbor Laboratory Press, Cold Spring Harbor, N.Y., 1986, the contents of which are incorporated herein by reference.

The knockout construct can be introduced into the ES cells by methods known in the art, e.g., those described in Sambrook et al. Suitable methods include, electroporation, microinjection, and calcium phosphate treatment methods.

The targeting construct to be introduced into the ES cell is preferably linear. Linearization can be accomplished by digesting the DNA with a suitable restriction endonuclease selected to cut only within the vector sequence and not within the VDR gene sequence.

After the introduction of the targeting construct, the cells are screened for the presence of the construct. The cells can be screened using a variety of methods. Where the marker gene is an antibiotic resistance gene, the cells can be cultured in the presence of an otherwise lethal concentration of antibiotic. Those cells that survive have presumably integrated the knockout construct. A southern blot of the ES cell genomic DNA can also be used. If the marker gene is a gene that encodes an enzyme whose activity can be detected (e.g., beta-galactosidase), the enzyme substrate can be added to the cells under suitable conditions, and the enzymatic activity can be analyzed.

To identify those cells with proper integration of the targeting construct, the DNA can be extracted from the ES cells using standard methods. The DNA can then be probed on a southern blot with a probe or probes designed to hybridize in a specific pattern to genomic DNA digested with particular restriction enzymes. Alternatively, or additionally, the genomic DNA can be amplified by PCR with probes specifically designed to amplify DNA fragments of a particular size and sequence such that, only those cells containing the targeting construct in the proper position will generate DNA fragments of the proper size.

Injection/Implantation of Embryos

Procedures for embryo manipulation and microinjection are described in, for example, Manipulating the Mouse Embryo (Cold Spring Harbor Laboratory Press, Cold Spring Harbor, N.Y., 1986, the contents of which are incorporated herein by reference). Similar methods are used for production of other transgenic animals. In an exemplary embodiment, mouse zygotes are collected from six week old females that have been super ovulated with pregnant mares serum (PMS) followed 48 hours later with human chorionic gonadotropin. Primed females are placed with males and checked for vaginal plugs on the following morning. Pseudo pregnant females are selected for estrus, placed with proved sterile vasectomized males and used as recipients. Zygotes are collected and cumulus cells removed. Furthermore, blastocytes can be harvested. Pronuclear embryos are recovered from female mice mated to males. Females are treated with pregnant mare serum, PMS, to induce follicular growth and human chorionic gonadotropin, hCG, to induce ovulation. Embryos are recovered in a Dulbecco's modified phosphate buffered saline (DPBS) and maintained in Dulbecco's modified essential medium (DMEM) supplemented with 10% fetal bovine serum.

Microinjection of a VDR targeting construct can be performed using standard micro manipulators attached to a microscope. For instance, embryos are typically held in 100 microliter drops of DPBS under oil while being microinjected. DNA solution is microinjected into the male pronucleus. Successful injection is monitored by swelling of the pronucleus. Recombinant ES cells can be injected into blastocytes, using similar techniques. Immediately after injection embryos are transferred to recipient females, e.g. mature mice mated to vasectomized male mice. In a general protocol, recipient females are anesthetized, paralumbar incisions are made to expose the oviducts, and the embryos are transformed into the ampullary region of the oviducts. The body wall is sutured and the skin closed with wound clips.

Screening for the Presence of the Targeting Construct

Transgenic (e.g., knockout) animals can be identified after birth by standard protocols. DNA from tail tissue can be screened for the presence of the targeting construct using southern blots and/or PCR. Offspring that appear to be mosaics are then crossed to each other if they are believed to carry the targeting construct in their germ line to generate homozygous knockout animals. If it is unclear whether the offspring will have germ line transmission, they can be crossed with a parental or other strain and the offspring screened for heterozygosity. The heterozygotes are identified by southern blots and/or PCR amplification of the DNA.

The heterozygotes can then be crossed with each other to generate homozygous transgenic offspring. Homozygotes may be identified by southern blotting of equivalent amounts of genomic DNA from mice that are the product of this cross, as well as mice that are known heterozygotes and wild type mice. Probes to screen the southern blots can be designed as set forth above.

Other means of identifying and characterizing the knockout offspring are known in the art. For example, northern blots can be used to probe the mRNA for the presence or absence of transcripts encoding either the gene knocked out, the marker gene, or both. In addition, western blots can be used to assess the level of expression of the gene knocked out in various tissues of these offspring by probing the western blot with an antibody against the protein encoded by the gene knocked out (e.g., the vitamin D receptor), or an antibody against the marker gene product, where this gene is expressed. Finally, in situ analysis (such as fixing the cells and labeling with antibody) and/or FACS (fluorescence activated cell sorting) analysis of various cells from the offspring can be performed using suitable antibodies to look for the presence or absence of the targeting construct gene product.

Other Transgenic Animals

The transgenic animal used in the methods of the invention can be a mammal; a bird; a reptile or an amphibian. Suitable mammals for uses described herein include: ruminants; ungulates; domesticated mammals; and dairy animals. Preferred animals include: goats, sheep, camels, cows, pigs, horses, oxen, llamas, chickens, geese, and turkeys. Methods for the preparation and use of such animals are known in the art. A protocol for the production of a transgenic pig can be found in White and Yannoutsos, Current Topics in Complement Research: 64th Forum in Immunology, pp. 88–94; U.S. Pat. Nos. 5,523,226; 5,573,933; PCT Application W093/25071; and PCT Application W095/04744. A protocol for the production of a transgenic rat can be found in Bader and Ganten, Clinical and Experimental Pharmacology and Physiology, Supp. 3:S81–S87, 1996. A protocol for the production of a transgenic cow can be found in Transgenic Animal Technology, A Handbook, 1994, ed., Carl A. Pinkert, Academic Press, Inc. A protocol for the production of a transgenic sheep can be found in Transgenic Animal Technology, A Handbook, 1994, ed., Carl A. Pinkert, Academic Press, Inc. All patents and references are incorporated herein by reference.

Uses of VDR Transgenic Mice

VDR misexpressing animals, e.g., mice, or cells can be used to screen treatments useful for treating VDR-related disorders, e.g., for treating skin disorders, immune system disorders or proliferative disorders, e.g., malignant tumors. The candidate treatment can be administered over a range of doses to the animal or cell. Efficacy can be assayed at various time points for the effects of the treatment on the disorder being evaluated.

Methods of the invention can be used to evaluate treatments for immune-related disorders and conditions. Such disorders include autoimmune disorders, hypersensitivities to the environment, e.g., allergies, anaphylaxis, allergic rhinitis (hay fever), bronchial asthma, atopic dermititis (eczema), urticaria (hives), transplant tissue rejection, and deficiencies of the immune system, e.g., AIDS.

Such treatments can be evaluated by determining the effect of the treatment on an immune-system-related parameter. Such parameters include the production, number, concentration, distribution, or activity of an immune system component. Examples of immune system components include immune cells, e.g., lymphocytes, immature or mature T cells, immature or mature B cells, or NK cells.

Other immune system components include molecules elaborated by, or which activate or inhibit, immune system cells. Examples include antibodies, e.g., IgG and IgM molecules, cytokines, e.g., pro-inflammatory cytokines or non-inflammatory cytokines, immune cell receptors, e.g., T cell or B cell receptors or co-receptors.

Other immune system parameters include the ability to reject allograft or xenograft tissue or the ability to recognize autologous or syngeneic tissue as self.

Other immune system parameters include the level of expression (at the gene or protein level) of immune system genes, e.g., genes which encode cytokines, e.g., interleukins, immune cell receptors, e.g., T or B cell receptors or co-receptors.

Methods of the invention can be used to evaluate treatments for proliferative disorders. Such disorders include cancer, e.g., squamus cell carcinomas, breast carcinomas, colon carcinomas, leukemia, Burkitt's lymphoma, pheochromocytomas, brain neoplasms, bronchogenic carcinomas, adenosarcomas, myelomas, chondrosarcomas, or osteogenic sarcomas; or non-malignant disorders, e.g., proliferative keratinocyte disorders, e.g., psoriasis, or alopecia and warts. Such treatments can be evaluated by determining their effect on a proliferation disorder-related parameter.

Such parameters include: cell growth; tumor growth, weight or invasiveness; life span; tissue morphology; weight; or the expression of a gene related to cell proliferation.

Methods of the invention can be used to evaluate treatments for hair-related disorders. Hair-related disorders include alopecia, e.g. common baldness (including pattern baldness) or chemotherapy induced alopecia; hypertrichosis or hirsutism. A hair-related condition includes unwanted facial or body hair. The evaluation can include determining the effect on: hair growth (in terms of the number, thickness, or growth rate of hairs), hair follicle morphology, or the pattern of hair growth.

Organ or tissue transplantation can involve the replacement of an injured or diseased tissue or organ. Often, the body recognizes the antigens in the transplanted tissue or organ (graft) as foreign and produces antibodies against them. This phenomenon is known as graft rejection.

Methods of the invention can be used to evaluate the effect of a treatment on the acceptance of a graft in a subject, e.g., a human.

Grafts can be allografts or xenografts (with regard to human recipients). Allografts can be partially or fully mismatched. E.g., matched allografts can be matched at one or more class I locus, one or more class II locus, or one or more minor antigen locus. Xenografts can be primate, e.g., monkey, or swine, e.g., miniature swine, or dog grafts. Grafts, allografts or xenografts, can be an organ, e.g., a lung, kidney, heart, liver, or endocrine tissue, e.g., pancreatic tissue, e.g., pancreatic islets, connective tissue, bone, skin, or bone marrow.

The treatment can be administered to a VDR misexpressing animal and the effect on a parameter related to graft acceptance evaluated. Such parameters include acceptance of the graft as measured, e.g., by survival time or functionality of a graft, e.g., kidney function in a kidney graft; or survival of the animal. The animal can also be administered a second treatment, e.g., an immunosuppressant, e.g., a broad spectrum immunosuppressant, e.g., cyclosporine, FK 506, rapamycin, muromonab-CD3, Azathioprine or a similar agent. The method can be used to find treatments which lessen the dosage of immunosuppressant needed to prevent graft rejection.

Methods of the invention can be used to evaluate treatments for autoimmune disorders. Autoimmune disorders include rheumatoid arthritis, e.g., juvenile rheumatoid arthritis, psoriatic arthritis, psoriasis, leprosy reversal reactions, erythema nodosum leprosum, autoimmune uveitis, multiple sclerosis, allergic encephalomyelitis, systemic lupus erythematosus, acute necrotizing hemorrhagic encephalopathy, idiopathic bilateral progressive sensorineural hearing loss, aplastic anemia, pure red cell anemia, idiopathic thrombocytopenia, polychondritis, scleroderma, Wegener's granulomatosis, chronic active hepatitis, myasthenia gravis, Stevens-Johnson syndrome, idiopathic sprue, lichen planus, Crohn's disease, Graves ophthalmopathy, sarcoidosis, primary biliary cirrhosis, diabetes, e.g., primary juvenile diabetes, dry eye associated with Sjögren's syndrome, uveitis posterior, or interstitial lung fibrosis.

The treatment can be administered to a VDR misexpressing animal or cell and the effect on a parameter related to immune function evaluated. Such parameters include: the presence, function, or morphology of T cells or their progenitors; the presence, function, or morphology of B cells or their progenitors; the presence, function, or morphology of natural killer cells or their progenitors; resistance to infection; life span, body weight, or the presence, function, or morphology of tissues or organs of the immune system; acceptance of a graft, preferably a syngeneic graft, e.g., syngeneic pancreatic cells; or, generally, the ability of the animal to recognize the animal's or cell's own antigens.

Methods of the invention can be used to study cells derived from the receptor ablated animals in order to define the mechanism of 1,25-dihydroxyvitamin D action on cell processes, e.g., proliferation and differentiation. For example, cells can be isolated from VDR misexpressing animals and used to identify agents that act downstream from 1,25-dihydroxyvitamin D in the VDR pathway or in independent pathways.

Accordingly, methods of the invention can be used to identify alternative pathways of 1,25-dihydroxyvitamin D action or agents that act downstream from 1,25-dihydroxyvitamin D in a keratinocyte. For example, pathways by which 1,25-dihydroxyvitamin D mediates its actions in normal keratinocytes can be examined and such pathways can be reconstituted in the knockout keratinocytes.

Similarly, methods of the invention can be used to identify alternative pathways of 1,25-dihydroxyvitamin D action or agents that act downstream from 1,25-dihydroxyvitamin D in a monocyte.

These approaches allow the discovery of new therapeutic agents that potentially have a greater therapeutic index than 1,25-dihydroxyvitamin D analogues in an in vivo setting.

Candidate Treatments

The candidate treatment, which is evaluated using methods described herein, can include: (a) the administration of a therapeutic agent (e.g., a drug, a chemical, an antibody, a protein, a nucleic acid or other substance) to a VDR misexpressing animal or cell; (b) the administration of a diet regimen to a VDR misexpressing animal; (c) the administration of ionizing radiation to a VDR misexpressing animal or cell. Any combination of the afore mentioned treatments can be administered to a VDR misexpressing animal or cell. The treatment can be administered prior to, simultaneously and/or after the onset of the disorder or condition, for which the candidate treatment is being evaluated. The therapeutic agent can be administered to a VDR misexpressing animal, orally, parenterally or topically.

EXAMPLES

Example 1
Generation of VDR Null Mice

The coding region of the rat VDR cDNA was reverse transcribed from ROS 12/2.8 cell mRNA and amplified by PCR to generate a probe for screening a 129/sv mouse genomic library. Two overlapping clones containing the sequences encoding the second zinc finger (exon 3) to the termination codon (exon 9) of the mouse VDR gene were isolated after screening 1.2×106 plaque forming units. A 5-kb XbaI fragment containing intronic sequences 5' to exon 3 (including part of the polylinker of the phage arm) and 3.5-kb XbaI fragment (including polylinker sequences from pUC 18) containing exons 4 and 5 of the receptor were subcloned into the XhoI and SalI sites, respectively, of the plasmid pNeo-TKXho (see FIG. 1). This targeting vector, shown in FIG. 1, was linearized with SalI and introduced into J1 embryonic stem (ES) cells by electroporation. After 8 days of selection with G418 (250 *g/ml) and gancyclovir (2 *M), ES cell colonies were isolated and screened by Southern analysis for the presence of homologous recombinants. Out of 600 ES cell clones screened, 17 cell lines that had undergone homogous recombination were identified, 16 of which had a single copy of the neomycin resistance gene. Chimeric mice were produced by injecting the recombinant ES cells into 3.5-day C57BL/6J mouse blastocysts and reimplanting the blastocysts into pseudopregnant females. Chimeras derived from two independent ES cell clones gave germline transmission. Homozygoud receptor ablated offspring from both clones showed identical phenotypes.

Example 2
Animal Maintenance

Figure 2:
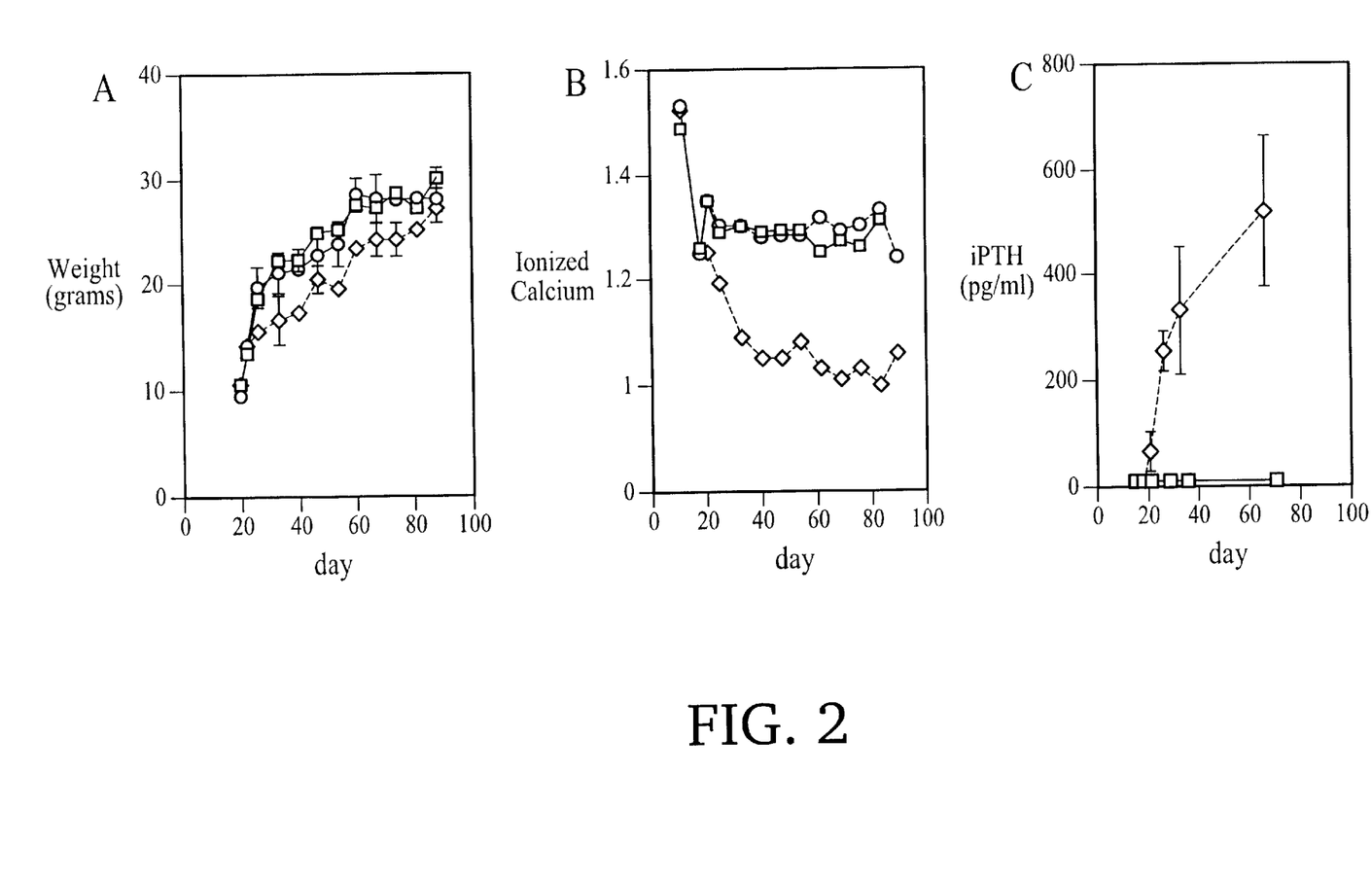
FIG. 2A is a graph showing that wild-type (squares) and heterozygous (circles) mice grow at a similar rate, and that homozygous (diamonds) mice gain weight more slowly after 21 days of age.
FIG. 2B is a graph showing that wild-type (squares) and heterozygous (circles) mice have similar levels of calcium, and that homozygous (diamonds) mice become hypocalcemic after 21 days of age.
FIG. 2C is a graph showing that parathyroid hormone levels in wild-type (squares) and heterozygous (circles) mice were less than 18 pg/ml at all stages and that parathyroid hormone levels in homozygous (diamonds) mice were indistinguishable from those of their heterozygous and wild-type litter mates at 15 and 19 days of age, but at 21 days of age began to rise.

Mice for generation of chimeras were obtained from Jackson Laboratories or Charles River Laboratories. All mice were kept in a virus-and parasite-free barrier facility. They were exposed to a 12-hour light/dark cycle and allowed free access to autoclaved water and chow. The Purina autoclavable rodent diet (5010) that they consumed contained 1% calcium, 0.67% phosphorus, and 4.4. units vitamin D per gram. The −/− animals were indistinguishable from their +/+ and +/− littermates at birth; however, from 24 days of age, they failed to grow as rapidly as their +/+ and +/− littermates and weighed 10% less by 91 days of age (see FIG. 2A). Their tibias and femurs were approximately 15% shorter than that of +/+ and +/− littermates. The +/− mice were phenotypically normal.

Example 3
Serum Chemistries

Parathyroid hormone levels were measured using a two-site assay for rat parathyroid hormone (P) (Corning). Ionized calcium levels were measured using a Ciba/Corning Ca2+/pH analyzer. Serum phosphorus values were measured with a Cobas Mira analyzer (Roche). The VDR −/− animals were normocalcemic until day 21, but they became progressively hypocalcemic from that point, maintaining ionized calcium levels approximately 25% lower than that of their +/− and +/+ liltermates (see FIG. 2B). Concomitant with the development of hypocalcemia, a progressive increase in serum immunoreactive PTH levels was observed from day 21 in the −/− mice (see FIG. 2C). Serum phosphorus levels were normal on day 16 (9.6+0.2 versus 9.5+0.9 mg/dl in the +/+ mice); however, correlating with the increase in immunoreactive PTH levels, the −/− mice became hypophosphatemic by day 21 (6.5+0.5 vs. 10.5+0.6 mg/dl).

Example 4
Tissue Histology and in Situ Hybridization

The thyroid, parathyroids, trachea, and heart were removed en bloc from day-70 littermates to facilitate orientation of the specimens, and to permit sectioning in the same plane. The specimens were fixed overnight in 4% formaldehyde in PBS, pH 7.2, processed, embedded in paraffin wax, and cut into 6-*m sections with a Leica RM 202 microtome. In situ hybridization was performed using an 35S-UTP-labeled PTH cRNA probe synthesized from a linearized plasmid containing exons 2 and 3 as well as the corresponding intervening sequence of the rat PTH gene. The sense probe was synthesized using Sp6 RNA polymerase, and the antisense probe was synthesized using T7 RNA polymerase. For in situ hybridization (described in Lee K. et al., 1995 Endocrinology 136:453–463, the contents of which are incorporated herein by reference), tissue sections were incubated at 65*C. for 45 minutes. Following deparaffinization and rehydration, the sections were fixed again with 4% paraformaldehyde in PBS for 15 minutes and treated sequentially as follows: 10 *g/ml proteinase K in PBS for 15 minutes; 4% paraformaldehyde in PBS for 10 minutes; PBS wash for 5 minutes; 0.2 N HCl for 10 minutes; PBS wash for 5 minutes; 0.1 M triethanolamine in 0.3% acetic anhydride for 10 minutes; and PBS wash for 5 minutes. The sections were then dehydrated with increasing concentrations of ethanol (70, 95, and 100%) and air-dried prior to hybridization.

Hybridization was carried out in a humidified chamber overnight at 55*C. in 50% formamide/10 mM Tris-HCl, pH 7.6/1×Denhardt's solution/10% dextran sulfate/600 mM NaCl/0.25% SDS/200 *g/ml tRNA. After hybridization the sections were rinsed in 5×SSC at 50*C. followed by a wash in 2×SSC/50% formamide at 50*C. for 30 minutes. The slides were then treated with 10 *g/ml RNase A in TNE (10 mM Tris-HCl, pH 7.6/500 mM NaCl/1 m EDTA) at 37*C. for 30 minutes, and washed sequentially as follows: TNE (37*C., for 10 minutes); 2×SSC (50*C., for 20 minutes); 0.2×SSC, twice (50*C., for 20 minutes). Following dehydration, the slides were air-dried and exposed to X-ray film for autoradiography. The slides were then dipped into NTB-2 emulsion (Kodak) and stored at 4*C. for exposure of the emulsion. After development the slides were counterstained with hematoxylin and eosin.

The femur, tibia, and fibula were isolated from 15- and 35-day-old mice and fixed in 4% formaldehyde for 18 hours at 4*C.. After contact radiography (FaxitronContact, Faxitron, F. R. G.) and dehydration, the undecalcified bones were embedded in methylmethacrylate and 5-*m sections were prepared on a rotation microtome (Jung, Heidelberg, F. R. G.) as described in Hahn M. et al., (1991) Virchows Arch. A Pathol. Anat. 418:1–7, the contents of which are incorporated herein by reference. Sections were stained with toluidine blue, von Kossa, or Goldner trichrome and evaluated using a Zeiss microscope (Carl Zeiss).

Examination of the parathyroid glands from day-70 mice revealed a marked increase in glandular size as well as in PTH mRNA content assessed by in situ hybridization. Based on the greatest diameter of the glands visualized on serial sections, and the number of sections in which the glands were visualized, the size of the parathyroid glands in the 70-day-old VDR ablated mice was increased more than 10-fold.

Contact radiography of the tibia at day 35 showed decreased cortical width along the diaphysis, as well as expansion and flaring of the growth plate, consistent with rickets. Histological analyses of the skeleton at this time showed decreased bone mineralization as assessed by von Kossa and Goldner trichrome staining. Examination of the growth plate at 35 days revealed marked disorganization with an increase in vascularity, matrix, and zone of hypertrophic chondrocytes. Contact radiography and histology of the tibiae and vertebrae from day-15 littermates failed to show a defect in bone mineralization; however, examination of the growth plate at this time revealed a 15% increase in the number of hypertrophic chondrocytes per column. The skeleton of the +/− animals was indistinguishable from that of the +/+ controls at both time points.

At the age of 4 weeks, the VDR −/− mice began to develop perioral and periorbital alopecia. This hair loss progressed to involve the entire body over the next 3 months. Alopecia was uniformly observed in the −/− mice but progressed more rapidly in the females than in the males. Histological analyses of the skin of the VDR −/− mice revealed dilatation of the hair follicles with formation of dermal cysts. The VDR is expressed in the outer root sheath keratinocytes and in the dermal papilla of the hair follicle. The development of secondary alopecia in the −/− mice shows that the VDR plays a key role in the hair cycle rather than in primary hair growth.

Gross and microscopic autopsy of mice sacrificed at 70 days of age revealed only the pathological changes described above.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of evaluating a treatment for modulating hair growth, comprising:

administering said treatment to a transgenic mouse having a disruption in each allele of a vitamin D receptor gene, wherein said transgenic mouse exhibits hair loss and lacks vitamin D receptor activity; and determining the effect of said treatment on modulating hair growth in said transgenic mouse, thereby evaluating said treatment for modulating hair growth.

2. The method of claim 1, wherein said treatment promotes hair growth.

3. The method of claim 1, wherein the effect of said treatment on modulating hair growth is determined by measuring a parameter selected from the group consisting of hair number, hair thickness, hair growth rate, hair follicle morphology and the pattern of hair growth.

4. The method of claim 1, wherein the disruption comprises insertion of a transgene.

5. The method of claim 1, wherein the disruption comprises deletion of the vitamin D receptor gene or a portion thereof.

6. The method of claim 1, wherein the disruption comprises removal of a DNA encoding all or part of a zinc-finger domain of the vitamin D receptor gene.

7. An isolated cell, or a purified preparation of cells from a transgenic mouse having a disruption in each of a vitamin D receptor gene, wherein said transgenic mouse exhibits hair loss and lacks vitamins D receptor activity.

8. The isolated cell, or purified population of cells of claim 7, wherein said cell is a keratinocyte cell.

9. The isolated cell, or purified population of cells of claim 7, wherein said cell is a dermal papilla cell.

10. An isolated cell, or a purified preparation of cells from a transgenic mouse having a disruption in each allele of a vitamin D receptor gene, wherein said transgenic mouse exhibits hair loss and lacks vitamin D receptor activity, and wherein said cell is selected from the group consisting of a keratinocyte cell and a dermal papilla cell.

* * * * *